United States Patent
Skerven

(10) Patent No.: US 9,457,383 B1
(45) Date of Patent: Oct. 4, 2016

(54) DISINFECTING MAT DEVICE

(71) Applicant: Virginia D. Skerven, Pensacola, FL (US)

(72) Inventor: Virginia D. Skerven, Pensacola, FL (US)

( * ) Notice: Subject to any disclaimer, the term of this patent is extended or adjusted under 35 U.S.C. 154(b) by 943 days.

(21) Appl. No.: 13/692,007

(22) Filed: Dec. 3, 2012

(51) Int. Cl.
*B08B 3/04* (2006.01)
*A47K 7/02* (2006.01)
*A47L 23/26* (2006.01)
*A47L 13/17* (2006.01)

(52) U.S. Cl.
CPC ............... *B08B 3/04* (2013.01); *A47K 7/026* (2013.01); *A47L 13/17* (2013.01); *A47L 23/266* (2013.01)

(58) Field of Classification Search
CPC ............... A47L 23/00–23/28; A47L 13/17; A47K 7/026; A47K 3/022; B08B 3/04
See application file for complete search history.

(56) References Cited

U.S. PATENT DOCUMENTS

| | | | | |
|---|---|---|---|---|
| 2,267,169 A | * | 12/1941 | Rast | A61H 35/006 128/200.21 |
| 2,274,739 A | * | 3/1942 | Rast | A61H 35/006 128/200.21 |
| 2,521,817 A | * | 9/1950 | Andresen | A47L 13/17 118/264 |
| 2,895,159 A | | 7/1959 | Ostrow | |
| 3,067,913 A | * | 12/1962 | Allison | A47L 23/24 222/211 |
| 3,115,653 A | | 12/1963 | Fresh et al. | |
| 3,165,773 A | | 1/1965 | Palpacelli | |
| 3,696,459 A | * | 10/1972 | Kucera | A47L 23/266 15/104.92 |
| 3,973,286 A | * | 8/1976 | Logan | A47K 3/022 15/104.92 |
| 4,027,355 A | | 6/1977 | Mead et al. | |
| D406,000 S | | 2/1999 | Hartranft | |
| 5,991,967 A | | 11/1999 | Williams | |
| 5,996,160 A | * | 12/1999 | Pruitt | A47L 23/24 15/104.92 |
| 6,223,379 B1 | * | 5/2001 | Martin | A47K 3/022 15/104.92 |
| 6,532,618 B2 | | 3/2003 | Koch | |
| 6,668,842 B1 | * | 12/2003 | Wilke | A47L 23/263 134/113 |
| 6,893,508 B2 | * | 5/2005 | Andrews | A47K 7/026 134/6 |
| 2009/0098031 A1 | * | 4/2009 | Crist | A47L 23/02 422/300 |
| 2010/0299828 A1 | * | 12/2010 | Shapiro | A47K 7/04 4/622 |

FOREIGN PATENT DOCUMENTS

DE 4103962 A1 * 8/1992 ........... A47L 23/266

OTHER PUBLICATIONS

DE 4103962—Machine Translation, Aug. 1992.*

* cited by examiner

*Primary Examiner* — Michael Kornakov
*Assistant Examiner* — Marc Lorenzi

(57) ABSTRACT

A disinfecting mat device cleans and sanitizes surfaces of objects coming into contact with the mat. The device includes a mat comprising a bottom wall, a perimeter wall, and an top wall defining an interior space of the mat. A compressible reservoir is positioned in the interior space and a fluid is positioned in the reservoir. An air chamber is positioned in the interior space. A plurality of ducts extends through a lower interior wall wherein each duct has an upper end in fluid communication with the air chamber and a lower end positioned adjacent to the reservoir. A plurality of tubes is in fluid communication with the reservoir extending through the top wall wherein each tube delivers the fluid in the reservoir to an upper surface of the top wall when the air chamber is compressed.

12 Claims, 4 Drawing Sheets

DISINFECTING MAT DEVICE

BACKGROUND OF THE DISCLOSURE

Field of the Disclosure

The disclosure relates to doorway mat devices and more particularly pertains to a new doorway mat device for cleaning and sanitizing surfaces of objects coming into contact with a floor surface as the object passes through a doorway.

SUMMARY OF THE DISCLOSURE

An embodiment of the disclosure meets the needs presented above by generally comprising a mat comprising a bottom wall, a perimeter wall, and an top wall defining an interior space of the mat. A compressible reservoir is positioned in the interior space and a fluid is positioned in the reservoir. An air chamber is positioned in the interior space. A plurality of ducts extends through a lower interior wall wherein each duct has an upper end in fluid communication with the air chamber and a lower end positioned adjacent to the reservoir. A plurality of tubes is in fluid communication with the reservoir extending through the top wall wherein each tube delivers the fluid in the reservoir to an upper surface of the top wall when the air chamber is compressed.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
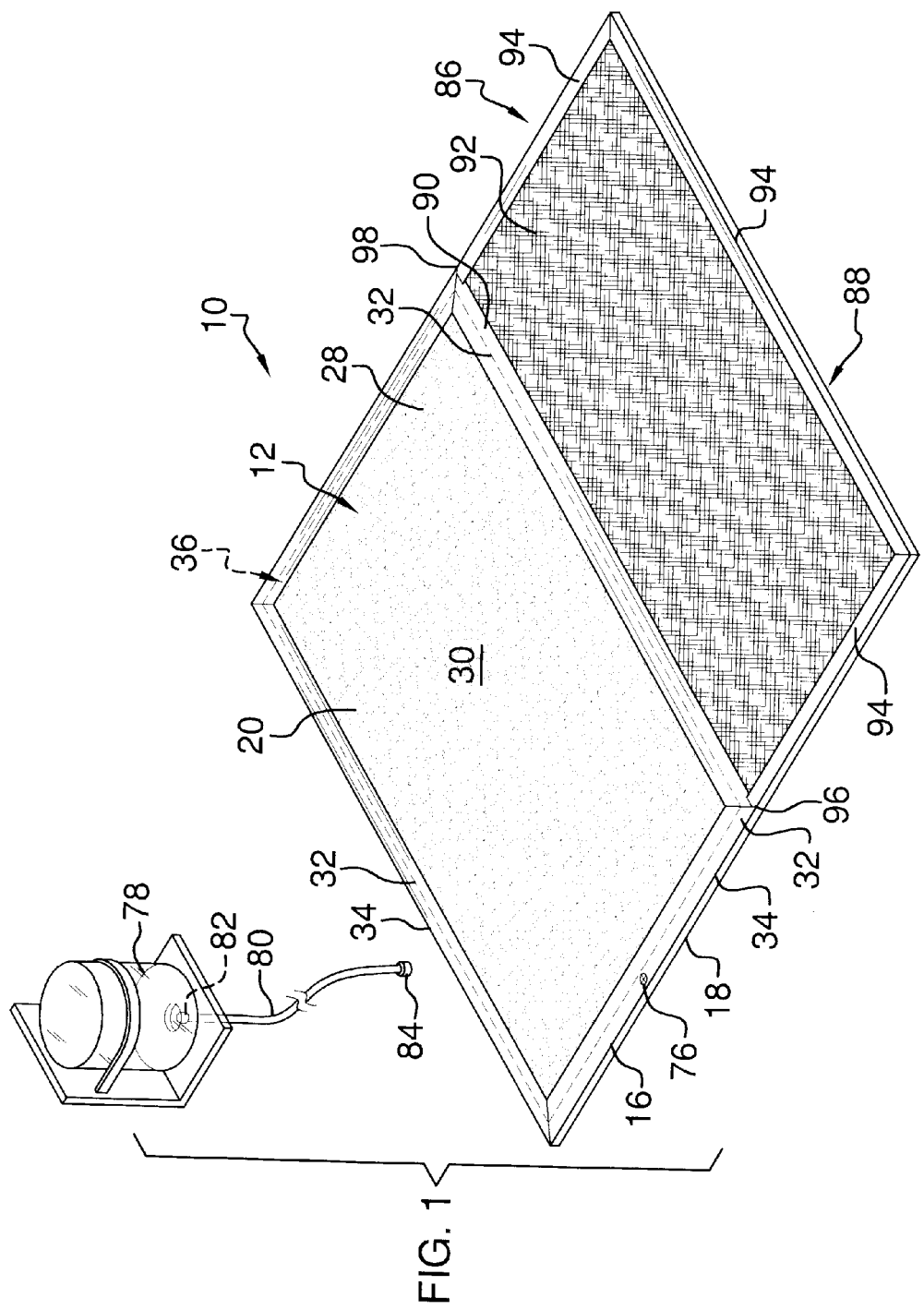
FIG. 1 is a top front side perspective view of a disinfecting mat device according to an embodiment of the disclosure.
Figure 3:
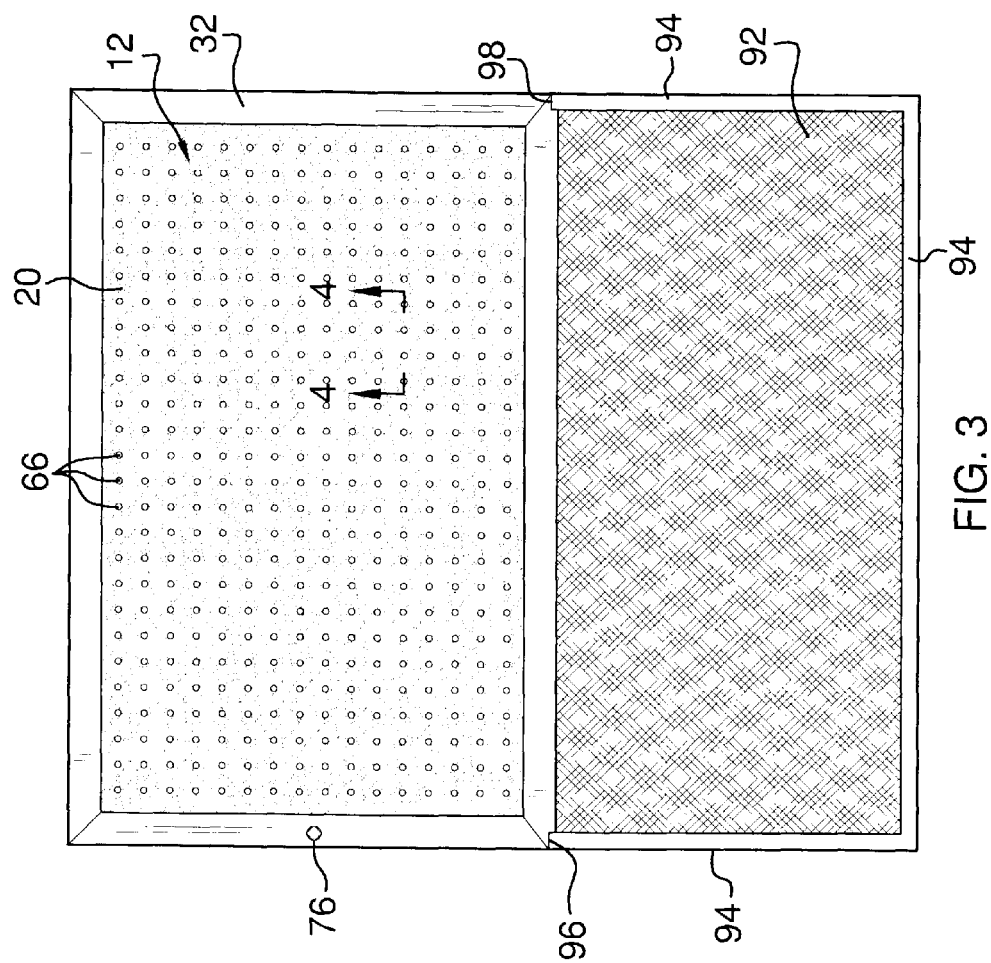
FIG. 3 is a top view of an embodiment of the disclosure.
Figure 2:
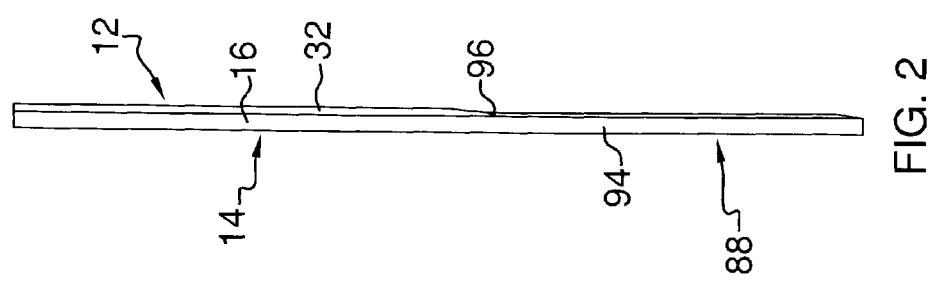
FIG. 2 is a side view of an embodiment of the disclosure.
Figure 4:
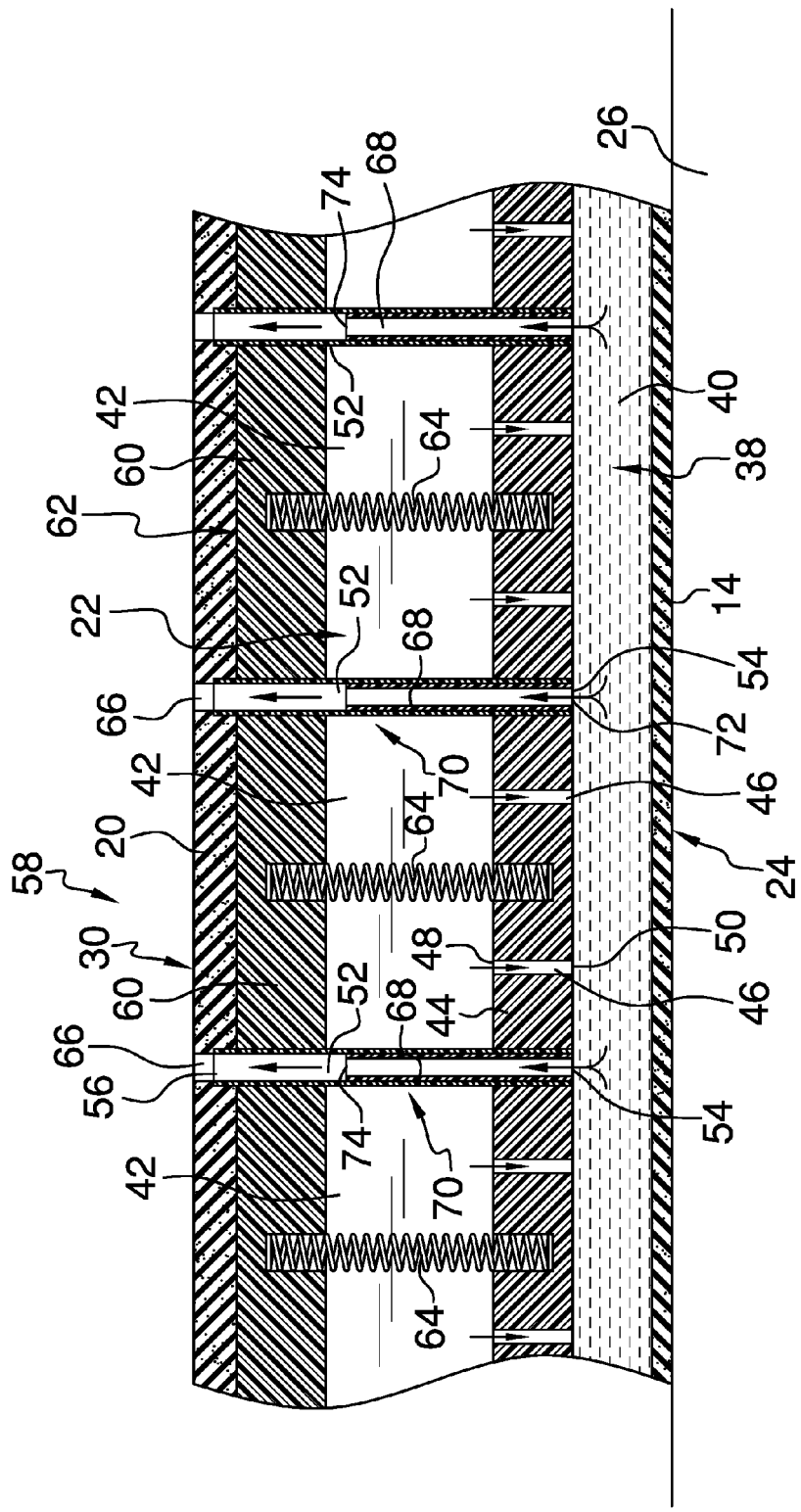
FIG. 4 is a cross-sectional view of an embodiment of the disclosure taken along line 4-4 of FIG. 3.
Figure 5:
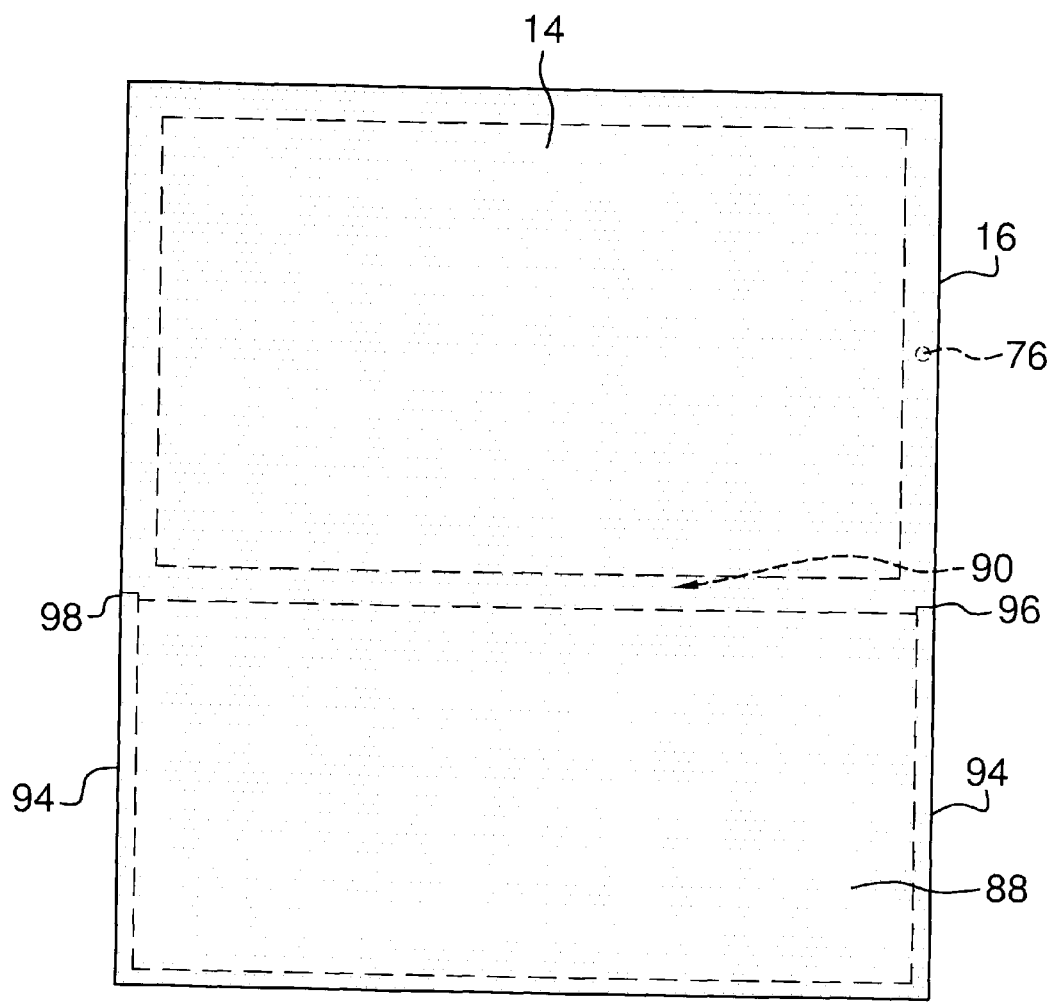
FIG. 5 is a bottom view of an embodiment of the disclosure.

With reference now to the drawings, and in particular to FIGS. 1 through 5 thereof, a new doorway mat device embodying the principles and concepts of an embodiment of the disclosure and generally designated by the reference numeral 10 will be described.

As best illustrated in FIGS. 1 through 5, the disinfecting mat device 10 generally comprises a mat 12 comprising a bottom wall 14, a perimeter wall 16 coupled to and extending upwardly from a perimeter edge 18 of the bottom wall 14, and a top wall 20 coupled to and extending inwardly from the perimeter wall 16 defining an interior space 22 of the mat 12. The bottom wall 14 may have a non-skid bottom surface 24 wherein the bottom wall 14 is configured to inhibit lateral movement of the mat 12 on a supporting surface 26. The top wall 20 may be constructed of a rubber material 28 wherein an upper surface 30 of the top wall 20 is configured to prevent slipping on the upper surface 30. A rim 32 is coupled to and extends inwardly from an upper edge 34 of the perimeter wall 16. The rim 32 overlaps an outer perimeter section 36 of the top wall 20. A compressible reservoir 38 is positioned in the interior space 22 and a fluid 40 is positioned in the reservoir 38. The fluid 40 may be designed to clean and disinfect.

An air chamber 42 is positioned in the interior space 22 between the top wall 20 and the bottom wall 14. A lower interior wall 44 is positioned in the interior space 22 between the air chamber 42 and the reservoir 38. A plurality of ducts 46 is provided. Each duct 46 extends through the lower interior wall 44 such that each duct 46 has an upper end 48 in fluid communication with the air chamber 42 and a lower end 50 positioned adjacent to the reservoir 38.

A plurality of tubes 52 is also provided. Each tube 52 has a lower end 54 in fluid communication with the reservoir 38. Each tube 52 has an upper end 56. The upper end 56 of each tube 52 is in fluid communication with ambient air 58 outside the interior space 22. Thus, each tube 52 delivers the fluid 40 in the reservoir 38 to the upper surface 30 of the top wall 20 when the air chamber 42 is compressed. Each tube 52 may be resiliently flexible.

An upper interior wall 60 is positioned in the interior space 22. The upper interior wall 60 is positioned between the air chamber 42 and a lower surface 62 of the top wall 20 wherein the air chamber 42 is positioned between the upper interior wall 60 and the lower interior wall 44. A plurality of biasing members 64 extends between the upper interior wall 60 and the lower interior wall 44. Each biasing member 64 urging the upper interior wall 60 away from the lower interior wall 44.

A plurality of openings 66 extends through the top wall 20. Each opening 66 is aligned with and coupled to an associated one of the tubes 52. The upper end 56 of the associated tube 52 is positioned in the opening 66. A plurality of stiff liners 68 may be provided. Each liner 68 is coupled to and positioned in an associated one of the tubes 52 wherein the liner 68 supports the associated tube 52 in an upright position 70. Each liner 68 has a bottom end 72 aligned with the lower end 54 of the associated tube 52. Each liner 68 also has a top end 74 positioned in spaced relationship to the upper surface 30 of the top wall 20 wherein the top end 74 of the liner 68 is prevented from extending through the top wall 20 past the upper surface 30 of the top wall 20.

A refill port 76 is coupled to the mat 12. The refill port 76 is in fluid communication with the reservoir 38. A refill tank 78 may be provided. A hose 80 has a first end 82 in fluid communication with the refill tank 78. The hose 80 has a second end 84 selectably couplable to the refill port 76 wherein fluid 40 in the refill tank 78 is selectively passable through the hose 80 into the reservoir 38.

A drying assembly 86 may be coupled to the mat 12 such that the drying assembly 86 extends from the mat 12. The drying assembly 86 comprises an extension section 88 of the bottom wall 14 extending outwardly from an interior edge 90 of the perimeter wall 16. An absorbent panel 92 is coupled to the extension section 88 of the bottom wall 14. A border wall 94 is coupled to the extension section 88 of the bottom wall 14. The border wall 94 has opposite ends 96,98 coupled to the perimeter wall 16. The border wall 94 extends around the absorbent panel 92 to prevent the absorbent panel 92 from moving relative to the mat 12.

In use, the mat 12 is positioned in a doorway or the like. Persons, animals or other objects such as carts or vehicles pass over the mat 12 wherein the fluid 40 is dispensed from the reservoir 38 onto whatever surface contacts the upper surface 30 of the top wall 20. The fluid 40 cleans and disinfects the surface contacting the upper surface 30 and putting pressure on the air chamber 42 to distribute the fluid 40 from the reservoir 38. Subsequent contact with the absorbent panel 92 facilitates drying of the cleaned and disinfected surface.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A disinfecting mat device comprising:
   a mat comprising a bottom wall, a perimeter wall coupled to and extending upwardly from a perimeter edge of said bottom wall, and a top wall coupled to and extending inwardly from said perimeter wall defining an interior space of said mat;
   a compressible reservoir positioned in said interior space;
   a fluid positioned in said reservoir;
   an air chamber being positioned in said interior space between said top wall and said bottom wall;
   a lower interior wall being positioned in said interior space between said air chamber and said reservoir; and
   a plurality of ducts, each said duct extending through said lower interior wall wherein each said duct has an upper end in fluid communication with said air chamber and a lower end positioned adjacent to said reservoir;
   a plurality of tubes, each tube having a lower end in fluid communication with said reservoir, each tube having an upper end, said upper end of said tube being in fluid communication with ambient air outside said interior space wherein each said tube delivers said fluid in said reservoir to an upper surface of said top wall when said air chamber is compressed;
   an upper interior wall being positioned in said interior space, said upper interior wall being positioned between said air chamber and a lower surface of said top wall wherein said air chamber is positioned between said upper interior wall and said lower interior wall, each of said tubes extending through said upper interior wall;
   a plurality of biasing members extending between said upper interior wall and said lower interior wall, each said biasing member urging said upper interior wall away from said lower interior wall; and
   a plurality of openings extending through said top wall, each said opening being aligned with and coupled to an associated one of said tubes, said upper end of said associated tube being positioned in said opening.

2. The device of claim 1, further comprising;
   each tube being resiliently flexible; and
   a plurality of stiff liners, each liner being coupled to and positioned in an associated one of said tubes wherein said liner supports said associated tube in an upright position.

3. The device of claim 2, further comprising each said liner having a bottom end aligned with said lower end of said associated tube.

4. The device of claim 3, further comprising each said liner having a top end positioned in spaced relationship to said upper surface of said top wall wherein said top end of said liner is prevented from extending through said top wall past said upper surface of said top wall.

5. The device of claim 1, further comprising said bottom wall having a non-skid bottom surface wherein said bottom wall is configured to inhibit lateral movement of said mat on a supporting surface.

6. The device of claim 1, further comprising a refill port coupled to said mat, said refill port being in fluid communication with said reservoir.

7. The device of claim 6, further comprising:
   a refill tank; and
   a hose having a first end in fluid communication with said refill tank, said hose having a second end selectably coupleable to said refill port wherein fluid in said refill tank is selectively passable through said hose into said reservoir.

8. The device of claim 1, further comprising said top wall being constructed of a rubber material wherein said upper surface is configured to prevent slipping on said upper surface.

9. The device of claim 1, further comprising a drying assembly coupled to and extending from said mat, said drying assembly comprising an extension section of said bottom wall extending outwardly from an interior edge of said perimeter wall, an absorbent panel being coupled to said extension section of said bottom wall.

10. The device of claim 9, further comprising a border wall coupled to said extension section of said bottom wall, said border wall having opposite ends coupled to said perimeter wall, said border wall extending around said absorbent panel.

11. The device of claim 1, further comprising a rim coupled to and extending inwardly from an upper edge of said perimeter wall, said rim overlapping an outer perimeter section of said top wall.

12. A disinfecting mat device comprising:
   a mat comprising a bottom wall, a perimeter wall coupled to and extending upwardly from a perimeter edge of said bottom wall, and a top wall coupled to and extending inwardly from said perimeter wall defining an interior space of said mat, said bottom wall having a non-skid bottom surface wherein said bottom wall is configured to inhibit lateral movement of said mat on a supporting surface, said top wall being constructed of a rubber material wherein an upper surface of said top wall is configured to prevent slipping on said upper surface;
   a rim coupled to and extending inwardly from an upper edge of said perimeter wall, said rim overlapping an outer perimeter section of said top wall;
   a compressible reservoir positioned in said interior space;
   a fluid positioned in said reservoir;

an air chamber being positioned in said interior space between said top wall and said bottom wall;

a lower interior wall being positioned in said interior space between said air chamber and said reservoir; and a plurality of ducts, each said duct extending through said lower interior wall wherein each said duct has an upper end in fluid communication with said air chamber and a lower end positioned adjacent to said reservoir;

a plurality of tubes, each tube having a lower end in fluid communication with said reservoir, each tube having an upper end, said upper end of said tube being in fluid communication with ambient air outside said interior space wherein each said tube delivers said fluid in said reservoir to said upper surface of said top wall when said air chamber is compressed, each tube being resiliently flexible;

an upper interior wall being positioned in said interior space, said upper interior wall being positioned between said air chamber and a lower surface of said top wall wherein said air chamber is positioned between said upper interior wall and said lower interior wall, each of said tubes extending through said upper interior wall;

a plurality of biasing members extending between said upper interior wall and said lower interior wall, each said biasing member urging said upper interior wall away from said lower interior wall;

a plurality of openings extending through said top wall, each said opening being aligned with and coupled to an associated one of said tubes, said upper end of said associated tube being positioned in said opening;

a plurality of stiff liners, each liner being coupled to and positioned in an associated one of said tubes wherein said liner supports said associated tube in an upright position, each said liner having a bottom end aligned with said lower end of said associated tube, each said liner having a top end positioned in spaced relationship to said upper surface of said top wall wherein said top end of said liner is prevented from extending through said top wall past said upper surface of said top wall;

a refill port coupled to said mat, said refill port being in fluid communication with said reservoir;

a refill tank;

a hose having a first end in fluid communication with said refill tank, said hose having a second end selectably coupleable to said refill port wherein fluid in said refill tank is selectively passable through said hose into said reservoir;

a drying assembly coupled to and extending from said mat, said drying assembly comprising an extension section of said bottom wall extending outwardly from an interior edge of said perimeter wall, an absorbent panel being coupled to said extension section of said bottom wall; and a border wall coupled to said extension section of said bottom wall, said border wall having opposite ends coupled to said perimeter wall, said border wall extending around said absorbent panel.

\* \* \* \* \*